(12) United States Patent
Ingram et al.

(10) Patent No.: US 7,731,065 B2
(45) Date of Patent: Jun. 8, 2010

(54) CLOSURE MEMBER

(75) Inventors: Simon James Ingram, Northampton (GB); Daljit Singh Ohbi, Bedford (GB); Richard Iain Harrison, Buckinghamshire (GB)

(73) Assignee: Consort Medical PLC, Hertfordshire (GB)

( * ) Notice: Subject to any disclaimer, the term of this patent is extended or adjusted under 35 U.S.C. 154(b) by 973 days.

(21) Appl. No.: 10/544,677

(22) PCT Filed: Jan. 27, 2004

(86) PCT No.: PCT/GB2004/000337

§ 371 (c)(1),
(2), (4) Date: Aug. 9, 2006

(87) PCT Pub. No.: WO2004/069664

PCT Pub. Date: Aug. 19, 2004

(65) Prior Publication Data

US 2007/0000950 A1 Jan. 4, 2007

(30) Foreign Application Priority Data

Feb. 4, 2003 (GB) .................................. 0302536.8

(51) Int. Cl.
*B65D 88/54* (2006.01)
*B65D 35/38* (2006.01)

(52) U.S. Cl. ........................ 222/494; 222/320; 222/491; 222/387; 222/319; 222/162; 128/200.14; 128/200.22; 128/200.24; 604/231; 604/218; 604/221; 604/184

(58) Field of Classification Search ................. 222/320, 222/43, 82, 153.13, 162, 321.3, 321.9, 405, 222/491–494, 319, 160, 386, 387; 128/200.11–200.22, 128/200.24, 203.12, 203.15, 203.22, 203.25; 604/231, 184, 194, 203, 218, 221, 222, 226
See application file for complete search history.

(56) References Cited

U.S. PATENT DOCUMENTS

| | | | | |
|---|---|---|---|---|
| 4,741,737 A | * | 5/1988 | Meyer et al. | ................. 604/140 |
| 4,830,284 A | * | 5/1989 | Maerte | ........................ 239/333 |
| 4,929,230 A | | 5/1990 | Pfleger | |
| 4,946,069 A | | 8/1990 | Fuchs | |
| 5,015,229 A | * | 5/1991 | Meyer et al. | ................... 604/90 |
| 5,181,658 A | | 1/1993 | Behar | |
| 5,257,726 A | * | 11/1993 | Graf et al. | ..................... 222/320 |
| 5,289,818 A | * | 3/1994 | Citterio et al. | ......... 128/200.14 |
| 5,299,718 A | | 4/1994 | Shwery | |
| 5,307,953 A | | 5/1994 | Regan | |

(Continued)

FOREIGN PATENT DOCUMENTS

EP 0486894 5/1992

(Continued)

OTHER PUBLICATIONS

Vacu Vin Bv, Tomorrow's Products For Consumers Today, "Vacuum Wine Saver" <URL: http://www.vacuvin.nl/instr-ws.htm> and <URLhttp://www.vacuvin.nl/con-comp.htm>, 2 pages, dated Aug. 28, 2003.

*Primary Examiner*—Kevin P Shaver
*Assistant Examiner*—Donnell Long
(74) *Attorney, Agent, or Firm*—Smith, Gambrell & Russell, LLP

(57) ABSTRACT

A container or vial (1) for a fluid, the container (1) comprising a casing defining an interior for storage of the fluid and a closure member (2). The closure member (2) comprises a body and at least one resilient projection (7) to seal in a storage condition an outlet of the casing, wherein upon an increase in the pressure of the interior of the container (1) the at least one resilient projection (7) is deflected to accommodate outflow of fluid through the outlet. The pressure in the interior of the container (1) may be increased by displacing the closure member (2) into the container (1) or by displacing some other element such as a bung (61, 82) into the container (1). The container (1) and closure member (2) may be used in a dispenser (90) and the closure element may be used in a valve (110).

33 Claims, 13 Drawing Sheets

U.S. PATENT DOCUMENTS

| | | | | |
|---|---|---|---|---|
| 5,368,201 A | * | 11/1994 | Fuchs | 222/162 |
| 5,427,280 A | * | 6/1995 | Fuchs | 222/320 |
| 5,431,155 A | | 7/1995 | Marelli | |
| 5,601,077 A | | 2/1997 | Imbert | |
| 5,655,689 A | * | 8/1997 | Fuchs et al. | 222/321.3 |
| 5,893,484 A | * | 4/1999 | Fuchs et al. | 222/83 |
| 6,095,376 A | | 8/2000 | Hennemann et al. | |
| 6,257,454 B1 | * | 7/2001 | Ritsche | 222/153.13 |
| 6,450,216 B1 | | 9/2002 | Stradella | |

FOREIGN PATENT DOCUMENTS

| | | |
|---|---|---|
| EP | 0526824 | 2/1993 |
| EP | 0827782 | 3/1998 |
| FR | 2635084 | 2/1990 |
| JP | 5-184674 | 7/1993 |
| JP | 10-57487 | 3/1998 |

* cited by examiner

CLOSURE MEMBER

The present invention relates to a container, such as a vial, sealed by a closure member and to a dispenser, such as a nasal dispenser, including a container or vial and a closure member. The invention further relates to a closure member and to a valve.

It is known from EP 0827782 to provide a metered dose of medicament in a sealed vial to be dispensed from a dispenser. A piercing element provided on a piston pierces the sealing member in the vial. The sealing member is then displaced into the vial forcing medicament out of the vial through the pierced opening in the sealing member. The medicament then passes through a channel formed in the piston and is expelled from the dispenser. A similar arrangement is also known from U.S. Pat. No. 5,307,953.

However, there are a number of problems associated with these known containers. In particular, the piercing element may generate particulates when puncturing the seal. These particulates may be dispensed with the medicament, or they may become lodged inside the dispenser and reduce its effectiveness. Furthermore, the requirement that a sharp piercing element be provided increases the risk of an accident occurring, for example during disposal of the dispenser. Further problems may also be encountered with the prior art devices when attempting to seal the vials, which are typically made of glass, as variations in the tolerances can result in an incomplete seal being formed.

The present invention at least in preferred embodiments attempts to address at least some of the problems associated with prior art devices.

According to a first aspect, the present invention provides a container for a fluid, the container comprising a casing defining an interior for storage of the fluid and a closure member, the closure member comprising a body and at least one resilient projection to seal in a storage condition an outlet of the casing, wherein upon an increase in the pressure of the interior of the container the at least one resilient projection is deflected to accommodate outflow of fluid through the outlet.

The increase in pressure of the interior of the container causes the resilient projection to deflect to facilitate the outflow of fluid without piercing the closure member. Thus, a piercing element is not required.

Advantageously, the provision of at least one resilient projection on the closure member compensates for any tolerance variances in the internal dimensions of the container and, thus, ensures that a good seal is formed.

Preferably, the resilient projection acts in sealing engagement with the casing of the container. In an unbiased condition, the at least one resilient projection preferably extends substantially radially outwardly from the body of the closure member. Furthermore, the at least one resilient projection preferably has a larger transverse dimension than the interior of the casing.

The at least one resilient projection preferably extends circumferentially around the body of the closure member.

The at least one resilient projection may be provided in a channel in the body of the closure member and may be a valve.

Preferably, three resilient projections are provided.

The container preferably also comprises at least one sealing portion which remains in sealing engagement with the casing.

The closure member and the at least one sealing portion may be connected to each other or may be separate from each other.

The closure member and/or the at least one sealing portion may be displaceable relative to the casing wherein in use, displacement of the closure member and/or the at least one sealing portion increases the pressure in the interior of the casing.

The closure member may comprise a channel for directing the outflow of fluid from the container. The channel preferably has at least one inlet port which is brought into fluid communication with an interior of the container when the at least one projection is deflected. The provision of a channel enables the outflow of fluid to be more readily controlled and/or directed. The channel is preferably pre-formed in the closure member.

The channel preferably comprises an interconnected axial conduit and transverse conduit. An inlet port is preferably provided at each end of the transverse conduit.

If the closure member and the at least one sealing portion are connected to each other, the at least one sealing portion preferably extends circumferentially around the body of the closure member. Preferably three sealing portions are provided.

The closure member is preferably made of an elastomer blend or thermoplastic elastomer but may also be made from any other suitable material known to those skilled in the art such as high-density polyethylene (HDP) or low density polyethylene (LDP) and, preferably, the elastomer has a Poisson's ratio of less than or equal to 0.5.

Most preferably, the closure member has a closed cell foam structure as this structure readily facilitates the deformation of the closure member under a top load and thereby enables the closure member to be displaced into the container relatively easily.

The container is preferably a vial suitable for medicament.

According to a second aspect of the present invention there is provided a dispenser, for example, a nasal dispenser, comprising a container according to the first aspect of the present invention and the dispenser further comprising a plunger or piston for displacing the closure member and/or the at least one sealing portion relative to the container.

The plunger is preferably provided with a delivery channel through which the outflow of fluid from the container is delivered.

The plunger and the closure member and/or the at least one sealing portion may be integrally formed.

Alternatively, the plunger may be formed separately from the closure member and/or the at least one sealing portion and in this arrangement the two components, preferably, sealingly engage in use. A conical flange is preferably provided on the plunger, closure member and/or the at least one sealing portion to sealingly engage with a recess formed in the other of said plunger, closure member and/or the at least one sealing portion.

According to a third aspect, the present invention provides a closure member suitable for sealing an outlet of a container, dispenser or a valve body, the closure member comprising a body and at least one resilient projection for acting in sealing engagement with a container, dispenser or a valve body, wherein said at least one resilient projection is deformable under pressure.

The deformation of the resilient projection advantageously allows fluid to be dispensed from the container without piercing the closure member.

The at least one resilient projection preferably extends circumferentially around the body of the closure.

Preferably, three resilient projections are provided.

The closure member preferably also comprises a channel for guiding the outflow of fluid from the container. The channel preferably comprises an interconnected axial conduit and transverse conduit. Preferably an inlet port is provided at each end of the transverse conduit. The channel is preferably preformed in the closure member.

The closure member may comprise at least one sealing portion for maintaining, in use, a seal between the sides of the closure member and the container. In use, the at least one sealing portion may advantageously reduce the likelihood of contamination of the medicament. The at least one sealing portion may also guide the closure member as it is inserted into the container.

The closure member may be formed integrally with a plunger. Alternatively, the closure member may be provided with a recess for sealingly engaging a conical flange provided on a plunger.

The closure member described herein is preferably made of an elastomer material, but may also be made from any other suitable material known to those skilled in the art such as high-density polyethylene (HDP) or low density polyethylene (LDP), all of which may provide the required resilience whilst maintaining a seal with the container. The Poisson's ratio of the elastomer is preferably less than or equal to 0.5 and, preferably, has a closed cell foam structure to facilitate easy deformation. Suitable elastomers include EPDM, polychloroprene, hydrogenated nitrile, butyl, halo-butyl, elastomer blends or an elastomer material that is FDA compliant, has low leachables and extractibles and is not swollen by the medicament fluid.

Alternatively, the closure member may include an elastomer blend, or a thermoplastic elastomer, such as dynamically cross-linked FPDM/PP, commonly known as Santoprene. Styrenic block copolymers such as block copolymers of styrene and butadiene or styrene, ethylene, butylene, copolymers are also suitable. Copolymers of polyester, polyether known as Hytrel or polyamide, polyether copolymers known as PEBAX can also be used.

The preferred closed cell foam structure can be created by the use of nitrogen releasing azodicarbonamode-blowing agents compounded in the material. The foam structure can also be created by using gas technology, such as injection of nitrogen in the moulding process.

According to a fourth aspect of the present invention there is provided a valve comprising a closure member according to the third aspect of the present invention, the closure member being provided in a hollow valve body with an internal surface for the at least one resilient projection of the closure member to sealingly engage when pressure is applied from one side of the hollow valve body. The at least one resilient projection is preferably arranged to deform under pressure applied from the other side of the hollow valve body to accomodate flow of fluid through the valve.

Preferred embodiments of the present invention will now be described, by way of example only, with reference to the accompanying drawings, in which.

Figure 1:
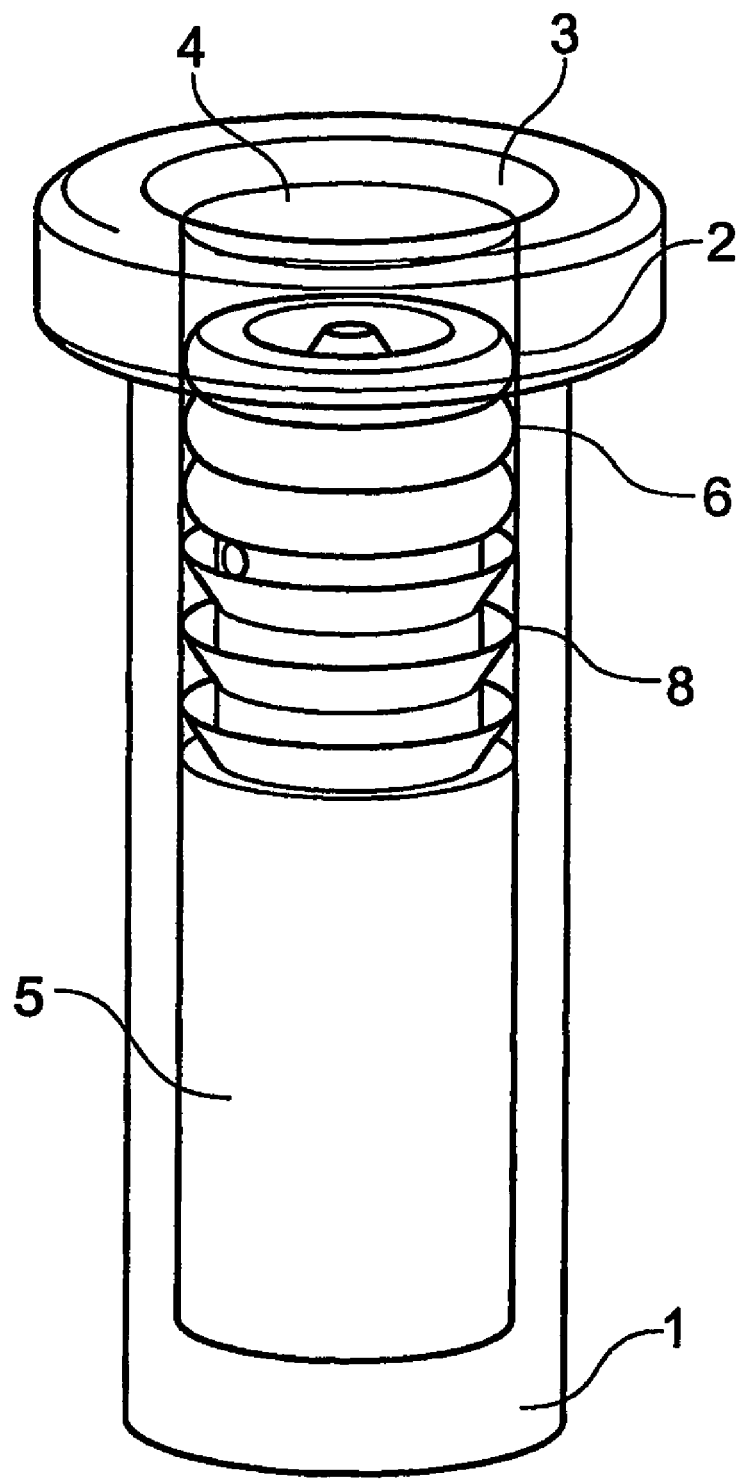
FIG. 1 shows a perspective view of a closure member in accordance with the present invention located in a vial.

A vial 1 having a closure member 2 located therein in accordance with the present invention is shown in FIG. 1. The vial 1 comprises a casing defining an outlet 3 and an interior 4. A metered dose of a liquid medicament 5 is filled in use in the interior 4 of the vial 1. The vial 1 is constructed from glass in known manner or an impermeable polymer, and the closure member 2 is moulded from a resilient elastomer material having a closed cell foam structure.

Figure 2:
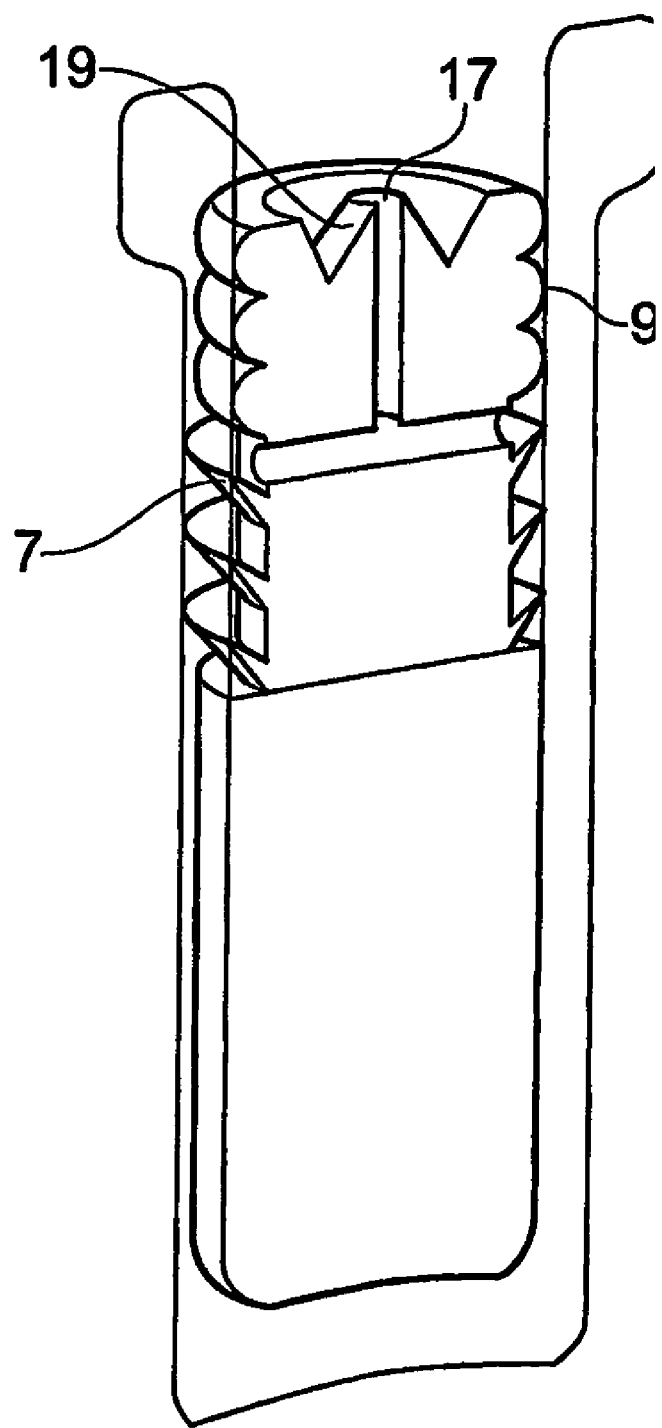
FIG. 2 shows a cross-sectional perspective view of the closure member and vial shown in FIG. 1.

The closure member 2 is circular in transverse cross-section and has an upper portion 6 and a lower portion 8. As shown in FIG. 2, three resilient sealing projections 7 extend outwardly around the circumference of the lower portion 8 of the closure member 2.

The upper portion 6 of the closure member 2 has three sealing portions 9 which extend outwardly around the circumference of the body of the closure member 2. The sealing portions 9 each have a convex cross-section to engage sealingly the interior 4 of the casing of the vial 1.

Prior to insertion into the vial 1 (i.e. in an unbiased condition), the resilient projections 7 extend substantially radially outwardly, and have a larger diameter than that of the interior 4 of the vial 1. Upon insertion of the closure member 2 into vial 1, the resilient projections 7 are deflected back on themselves. The rearward deflection and consequent biasing of the resilient projections 7 helps to maintain a good seal between the closure member 2 and the vial 1 and also to retain the closure member 2 in place.

A channel 11 is pre-formed in the closure member 2 in the shape of an inverted "T". The channel 11 has two inlet ports 13, 15 located between the resilient projections 7 and the sealing portions 9 which are joined by a first conduit. A second conduit connects to a mid-point of the first conduit and extends axially up to an outlet 17 formed in the upper end of the closure member 2. The first and second conduits constitute channel 11. A circular recess 19 is formed in the upper surface of the closure member 2 around the outlet 17.

The assembly of the vial 1 will now be described. The metered dose of medicament 5 is introduced into the vial 1 and the closure member 2 is then inserted as a push-fit into the open end of the vial.

The insertion of the projections 7 into the vial creates a seal and the displacement of the closure member 2 further into the vial 1 results in an increase in pressure in the interior 4 of the vial 1.

The increased pressure causes the resilient projections 7 to deflect creating a leak path to the atmosphere, via the channel 11. Any excess fluid or air initially present in the vial 1 is expelled through this leak path. The expulsion of the fluid or air reduces the pressure inside the vial 1 and the projections 7 then return to their original positions sealingly engaging the sidewalls of the vial 1.

The closure member 2 is inserted into the vial 1 until the sealing portions 9 are located therein, as shown in FIG. 1. The vial 1 is then ready for use.

The sealing portions 9 provide a primary seal for the vial 1, and the resilient projections 7 provide a secondary seal capable of deflecting under pressure to facilitate the outflow of fluid. As the resilient projections 7 do not provide the only seal for the vial 1 they may be more flexible to facilitate deflection in response to a lower pressure in the interior 4 of the vial 1. Advantageously, therefore, the force required to displace the closure member 2 relative to the vial 1 may be reduced. Furthermore, the configuration of the sealing portions 9 may be varied independently to create the desired seal for the vial 1, without affecting the functionality of the resilient projections 7.

In arrangements not having sealing portions 9, the resilient projections 7 provide the only seal for the vial 1. To ensure that an adequate seal is created the resilient projections 7 are typically less flexible so that they are biased more vigorously against the sidewalls of the vial 1. Accordingly, a larger pressure in the interior 4 of the vial 1 is required to cause them to deflect. Thus, the force required to displace the closure member 2 relative to the vial 1 is greater.

The dispensing of the medicament 5 from the vial 1 will now be described. The closure member 2 is displaced downwardly into the vial 1 and, because the vial 1 is sealed by the projections 7, there is again an increase in pressure in the interior 4. The increased pressure causes the resilient projections 7 to deflect and create a pathway from the interior 4 of the vial 1 to the inlet ports 13, 15 of the channel 11.

Continued displacement of the closure member 2 causes the medicament 5 to be displaced from the vial 1 through the pathway formed by the deflection of the resilient projections 7, through the inlet ports 13, 15 and out through the outlet 17 of the channel 11. As the closure member 2 is displaced downwardly, the sealing portions 9 maintain a seal between the closure member 2 and the vial 1 and thereby ensure that the medicament 5 is expelled only through the channel 11. The closure member 2 is displaced into the vial 1 until the lower surface thereof abuts the base of the vial 1.

Figure 3:
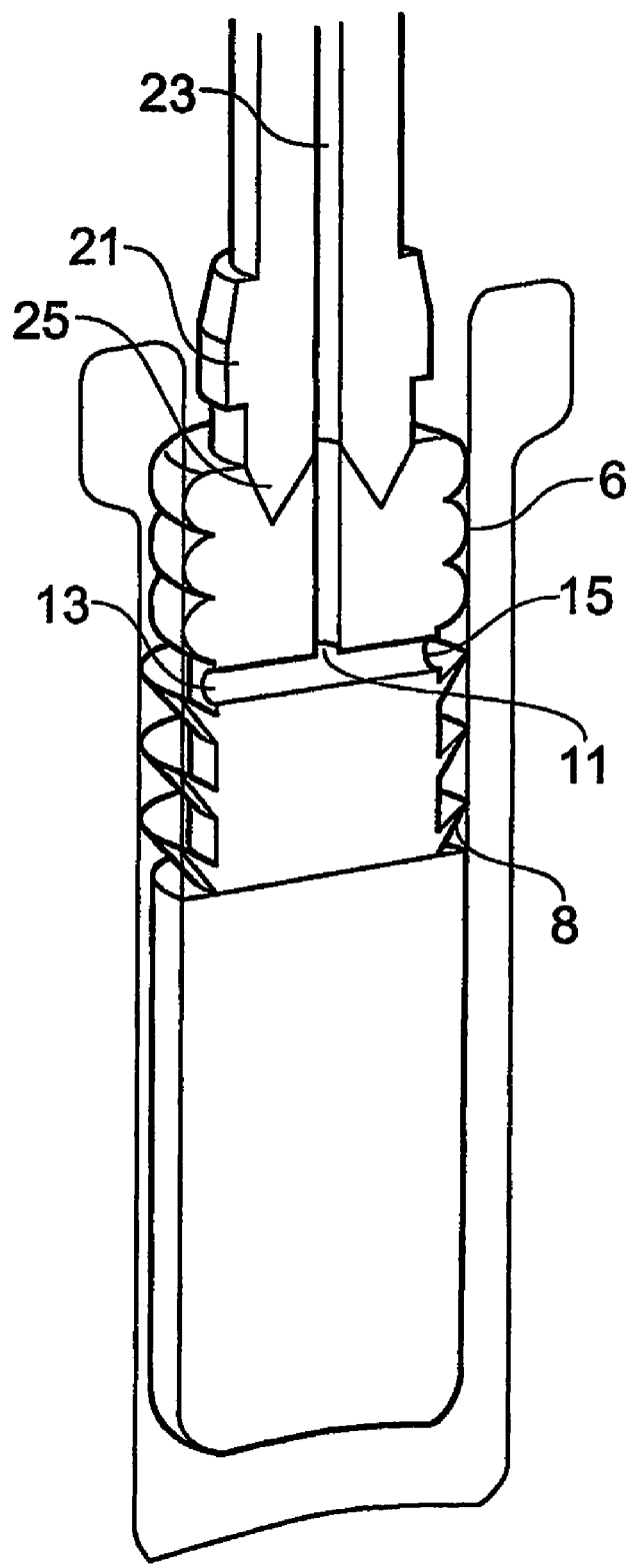
FIG. 3 shows a cross-sectional view of the closure member of FIG. 1 and a plunger in accordance with the present invention.

As shown in FIG. 3, a plunger 21 is employed to displace the closure member 2 downwardly. The plunger 21 has a delivery channel 23 formed therethrough and an annular conical projection 25 formed at the distal end thereof. The annular conical projection 25 is arranged to engage sealingly the circular recess 19 provided in the upper end of the closure member 2 and to align the outlet 17 with the delivery channel 23.

Figure 4:
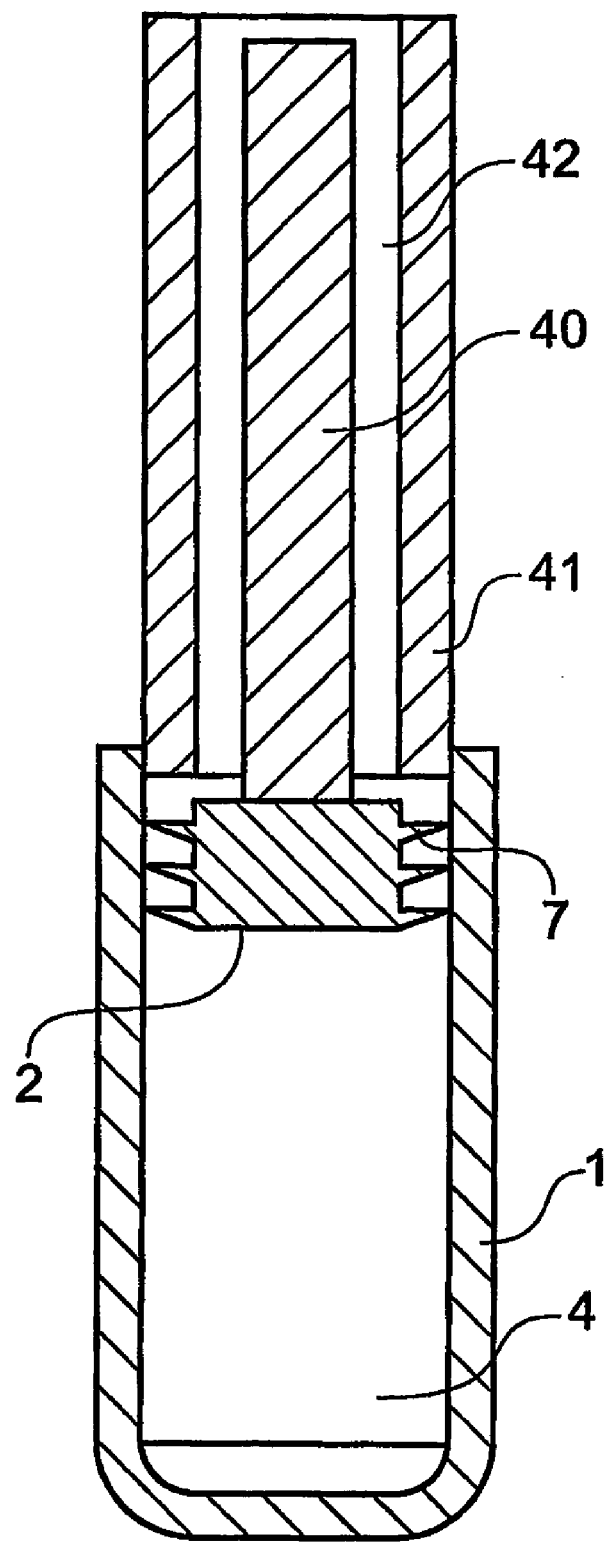
FIGS. 4 to 8 show schematic cross-sectional views of further closure member arrangements.

As shown in FIG. 4, the closure member 2 may comprise just the lower portion 8 as shown in FIGS. 1 to 3 with at least one resilient sealing projection 7 extending outwardly around the circumference of the closure member body. The closure member 2 is shown in FIG. 4 provided on a plunger 40. In this example the plunger 40 is integrally formed with the closure member 2. However the plunger 40 could be separate from the closure member 2 and could be arranged to engage sealingly the closure member 2 as for example in the example of FIG. 3. The plunger 40 is surrounded by a concentric sleeve 41 such that an outlet channel 42 is provided therebetween. As in the examples of FIGS. 1 to 3, the vial 1 is provided with a metered dose of fluid medicament. To dispense the medicament from the vial, the plunger 40, closure member 2 and concentric sleeve 41 are displaced downwardly into the vial 1. As in the devices of FIGS. 1 to 3, as the vial 1 is sealed by the projections 7 there is an increase in pressure in the interior 4 of the vial 1 as the closure member 2 is displaced downwardly into the vial 1. The increased pressure causes the resilient projections 7 to deflect upwardly and create a pathway from the interior 4 of the vial 1 to the outlet channel 42. As the plunger 40, closure member 2 and concentric sleeve 41 are all displaced downwardly into the vial 1, ullage is reduced.

Figure 5:
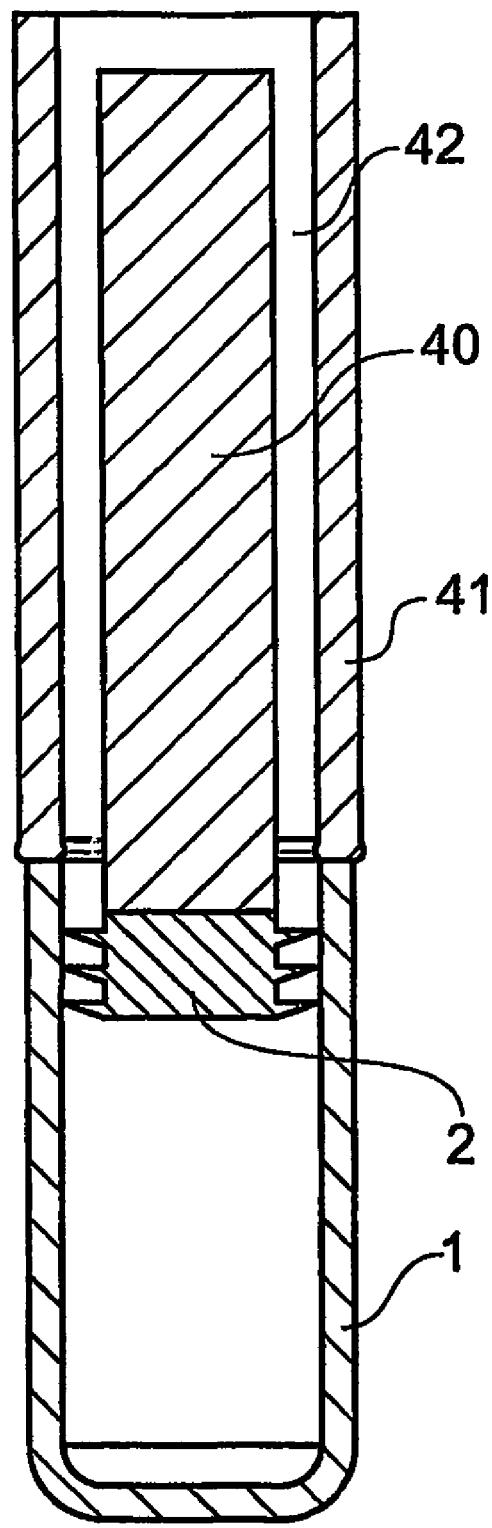

The example shown in FIG. 5 is similar to the example shown in FIG. 4 except that the concentric sleeve 41 is attached to the vial 1 so that when the plunger 40 and closure member 2 are displaced downwardly into the vial 1, the concentric sleeve 41 remains fixed to the vial. Like the example shown in FIG. 4, medicament is expelled through the outlet channel 42 between the plunger 40 and concentric sleeve 41.

Figure 6:
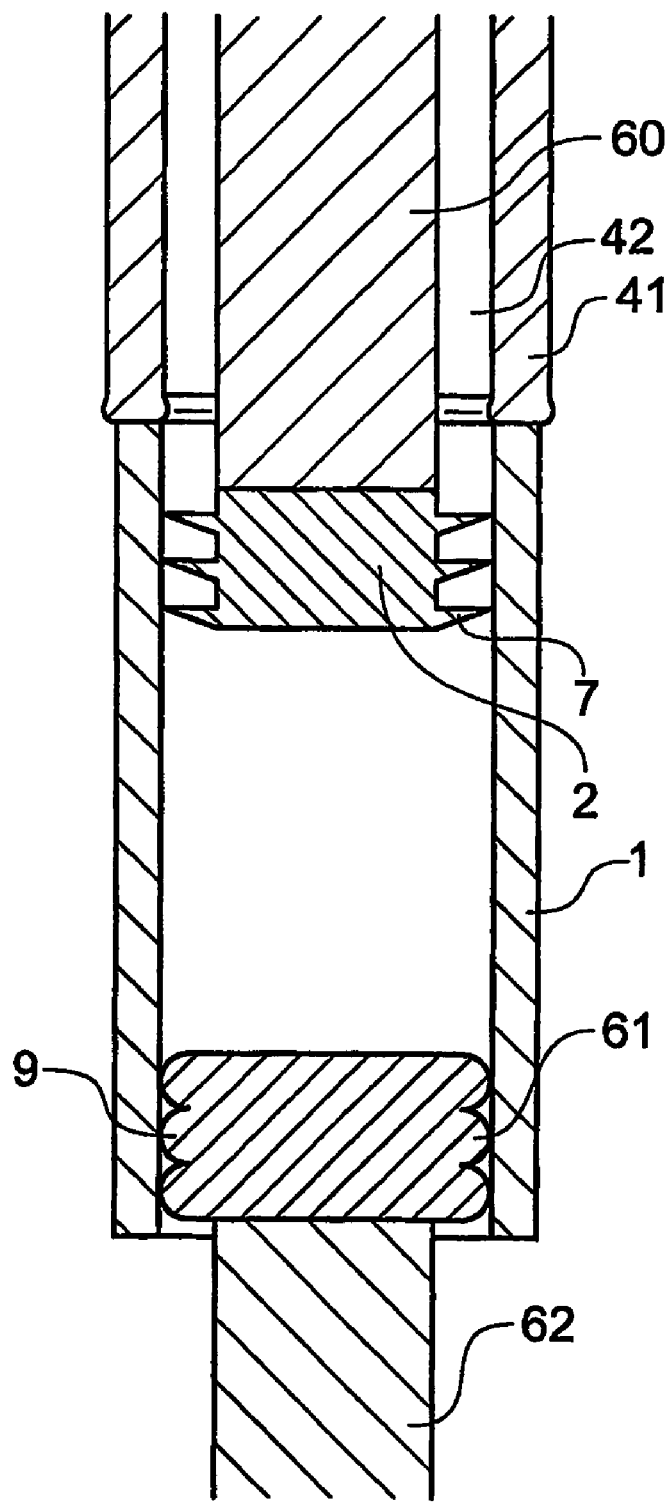

The example shown in FIG. 6 is similar to that of FIG. 5 except that the closure member 2 is provided on a fixed support member 60 and the vial 1 is sealed at its other end by a bung 61 provided on a plunger 62. The bung 61 may be similar to the upper portion 6 described with reference to FIGS. 1 to 3 and in this example comprises three sealing portions 9 which extend outwardly around the circumference of the bung 61 with each sealing portion 9 having a convex cross-section to engage sealingly with the interior of the vial 1. As in the previous examples, the vial 1 is provided with a metered dose of fluid medicament. To dispense the medicament from the vial 1, the bung 61 and plunger 62 are displaced upwardly into the vial 1 with the closure member 2 remaining fixed relative to the vial 1. As the vial is sealed by the projections 7 of the closure member 2 and the bung 61, there is an increase in pressure in the interior of the vial 1 as the bung 61 is displaced upwardly into vial 1. The increase in pressure causes the resilient projections 7 to deflect upwardly and create a pathway from the interior of the vial to the outlet channel 42.

Figure 7:
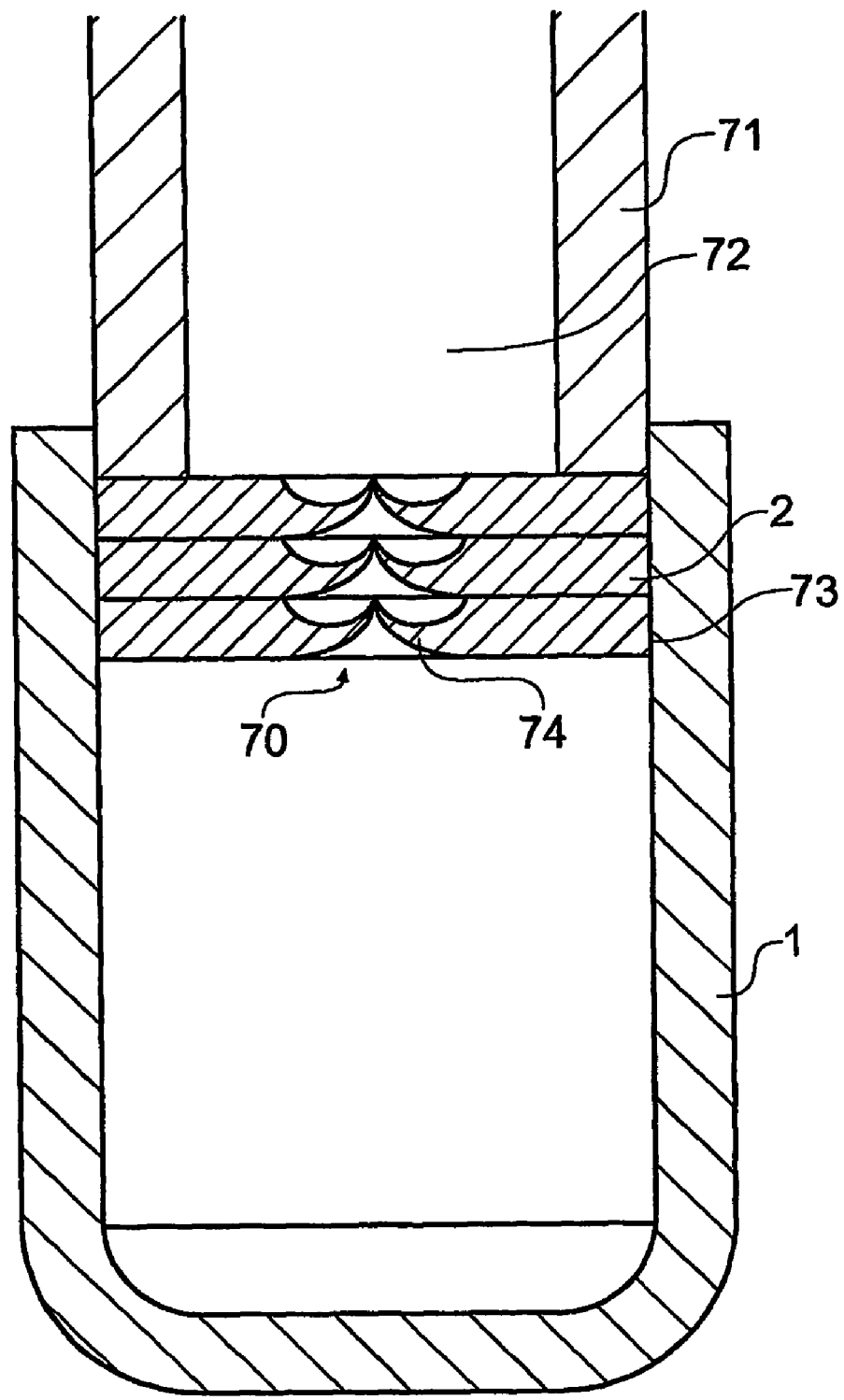

Rather than the at least one resilient projection 7 being provided around the circumference of the closure member 2, the at least one resilient projection may be provided in a channel 70 in the closure member 2 as shown in FIG. 7. In this example the closure member 2 is provided on a plunger 71 with an internal outlet channel 72. The outside surface 73 of the closure member 2 seals against the inside surface of the vial 1. The closure member 2 is provided with one or more internal resilient projections 74 which may act as a valve such as a duck-bill valve to seal the interior of the vial 1. As in the previous examples, the vial 1 is provided with a metered dose of fluid medicament. To dispense the medicament from the vial 1, the plunger 71 and closure member 2 are displaced downwardly into the vial 1 with the outside surface 73 of the closure member 2 maintaining a seal against the inside surface of the vial 1 which increases the pressure in the interior of the vial 1. The increase in pressure causes the internal resilient projections 74 to deflect upwardly and create a pathway from the interior of the vial 1 to the outlet channel 72.

Figure 8:
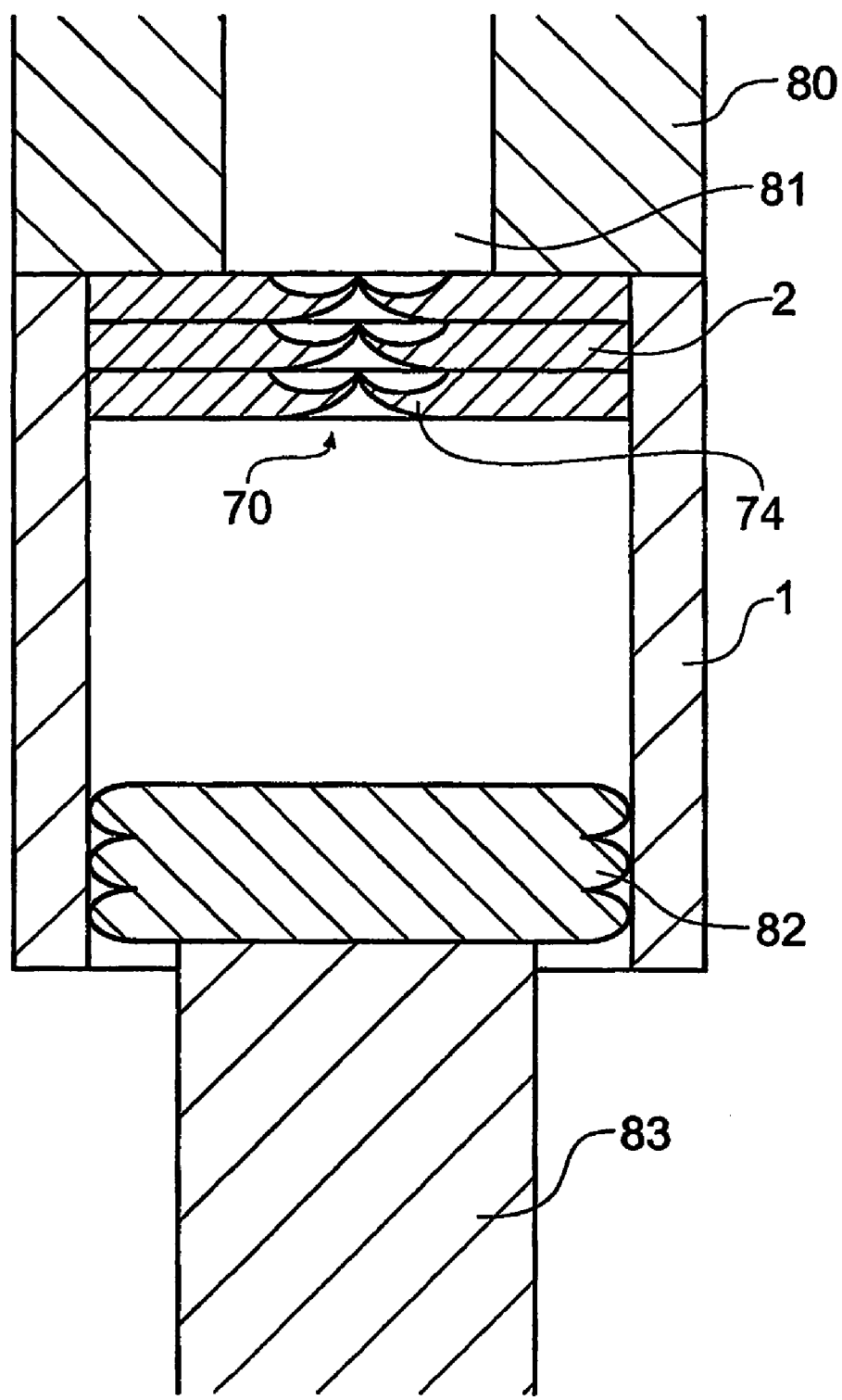

The example shown in FIG. 8 is similar to that of FIG. 7 except that the closure member 2 is provided on a fixed support member 80 with an internal outlet channel 81 and the vial is sealed at its other end by a bung 82 provided on a plunger 83. The bung 82 may be similar to the bung 61 shown in FIG. 6. As in the previous examples, the vial 1 is provided with a metered dose of fluid medicament. To dispense the medicament from the vial 1, the bung 82 and plunger 83 are displaced upwardly into the vial 1 with the closure member 2 remaining fixed relative to the vial 1. The pressure increases in the interior of the vial 1 as the bung 82 is displaced upwardly into the vial 1 until the internal resilient projections 74 deflect upwardly and create a channel 70 from the interior of the vial 1 to the outlet channel 81.

The examples of FIGS. 7 and 8 may be provided with a suitable elongate portion in their internal outlet channels 72, 81 to aid mechanical break-up of the ejected fluid medicament.

Figure 9:
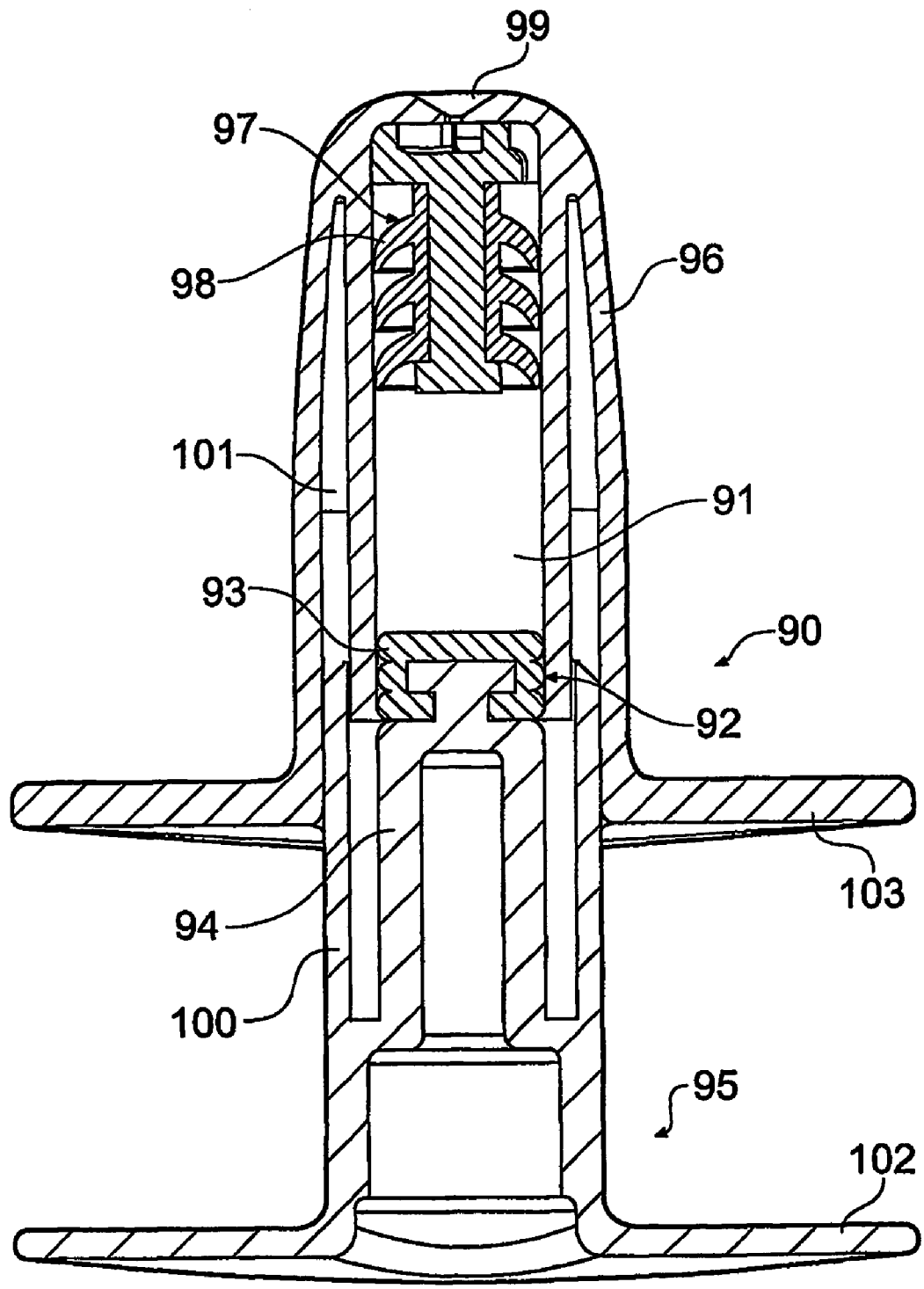
FIG. 9 shows a schematic cross-sectional view of a dispenser incorporating the present invention.

The vial 1 in combination with the closure member 2 may be used, for example, in a dispenser such a nasal dispenser. FIG. 9 shows an example of a dispenser 90 illustrating the present invention. The dispenser 90 includes or forms a container or vial 91 to be provided with a dose of fluid medicament. The vial 91 is sealed at its lower end by a bung 92. The bung 92 in this example is similar to that shown in FIGS. 6 and 8 and comprises three sealing portions 93 which extend outwardly around the circumference of the bung 92 with each sealing portion 93 having a convex cross-section to engage sealingly with the interior of the vial 91. The bung 92 is provided on a plunger 94 forming part of a base 95 of the dispenser 90. A closure member 97 is provided at the upper end of the vial 91. The closure member 97 has three resilient projections 98 extending outwardly around the circumference of the closure member body to seal against the inside surface of the vial 1.

The vial 91 is formed as part of an actuator 96 of the dispenser 90. The actuator 96 has an outlet 99 through which medicament is dispensed after having been discharged from the vial 91. The base 95 is provided with a sleeve 100 to be received in a recess 101 in the actuator 96 to guide the base 95 upon insertion into the actuator 96.

The dispenser 90 may be actuated by a user displacing the base 95 upwardly with respect to the actuator 96 using finger supports 102, 103 on the base 95 and actuator 96 respectively. Displacing the base 95 upwardly with respect to the actuator 96 forces the bung 92 upwardly into the vial 91. As in the previous examples, as the vial 91 is sealed by the resilient projections 98 of the closure member 97, there is an increase in pressure in the interior of the vial 91 as the bung 92 is displaced upwardly relative to the actuator 96. The increased pressure causes the resilient projections 98 to deflect upwardly and create a pathway from the interior of the vial 91 to the outlet 99.

The dispenser may be provided with a device for forming a spray for delivery of the medicament to the user.

After the dispenser 90 has been emptied of medicament, it is difficult to pull the base 95 and actuator 96 apart because the closure member 97 acts as a one-way valve preventing air from entering the vial 91.

This dispenser does not require a piercing element to expel drug and so significantly reduces the risk of producing particulates and the risk of injury. The dispenser also has a very smooth operation due to the pre-compression not being produced by breaking snaps or the use of piercing elements and very low ullage.

FIGS. 10 to 13 show examples of a number of valves embodying the invention. These valves provide an excellent seal to prevent fluid from the lower portion of the valve from passing through to the upper portion of the valve as illustrated, and yet require only a small pressure or force applied to the valve to enable fluid to be passed from the upper portion of the valve to the lower portion of the valve. The valves illustrated in FIGS. 10 to 13 are check valves as may be used in the medical field for example for use in the insertion and removal of fluids into or out of animals or humans.

Figure 10:
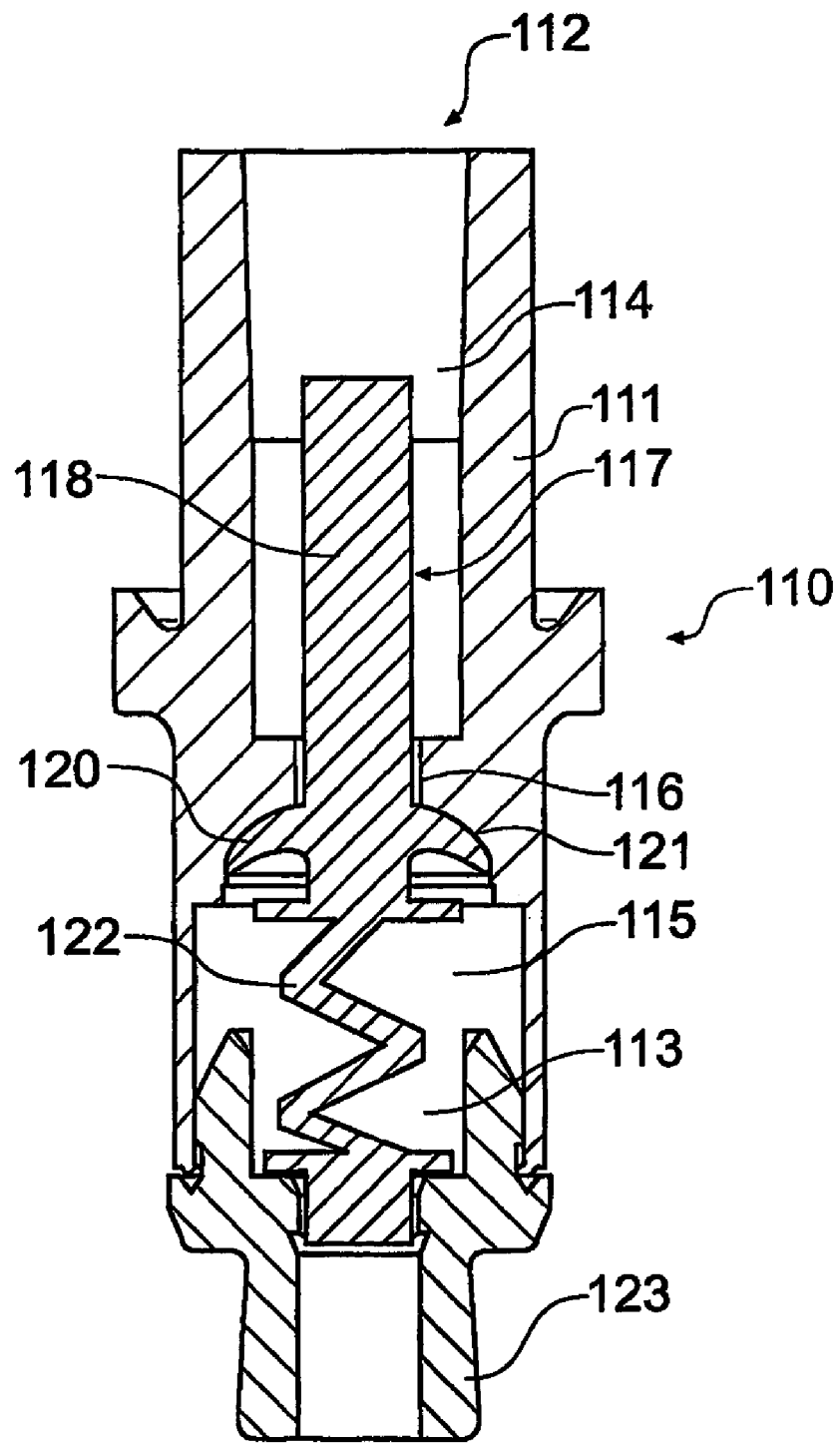
FIGS. 10 to 13 show schematic cross-sectional views of valves in accordance with the present invention.

As shown in FIG. 10, the valve 110 comprises a hollow body 111 with an open end 112 at an upper end of the body 111 and an open end 113 at a lower end of the body 111. A continuous bore 114, 115 runs from open end 112 to open end 113 via aperture 116. The upper portion of bore 114 is tapered with a Luer taper such that the inner diameter of bore 114 slightly decreases towards the aperture 116.

A core 117 acting as a closure member is contained within the body 111 and comprises a generally cylindrical body member 118, with a resilient sealing projection 120 in this example extending circumferentially outwardly from the core 117, to engage a portion 121 of an inner surface of the bore. The core 117 is biased upwards in the example shown in FIG. 10 by means of a spring 122. The spring 122 biases the closure member 120 into sealing contact with a portion 121 of an inner surface of the bore.

When fluid is passed into the upper bore 114, the increased pressure from this fluid deflects the resilient projection 120 downwardly and creates a pathway from the upper portion of the bore 114 to the lower portion of the bore 115. The core 117 may also be pushed downwards against the biasing of spring 122 to accommodate a greater flow of fluid.

A cap 123 provided on the lower portion of the hollow body 111 is also displaced by the passage of fluid into the lower portion of the bore 115 to enable fluid to pass out of the valve.

Figure 11:
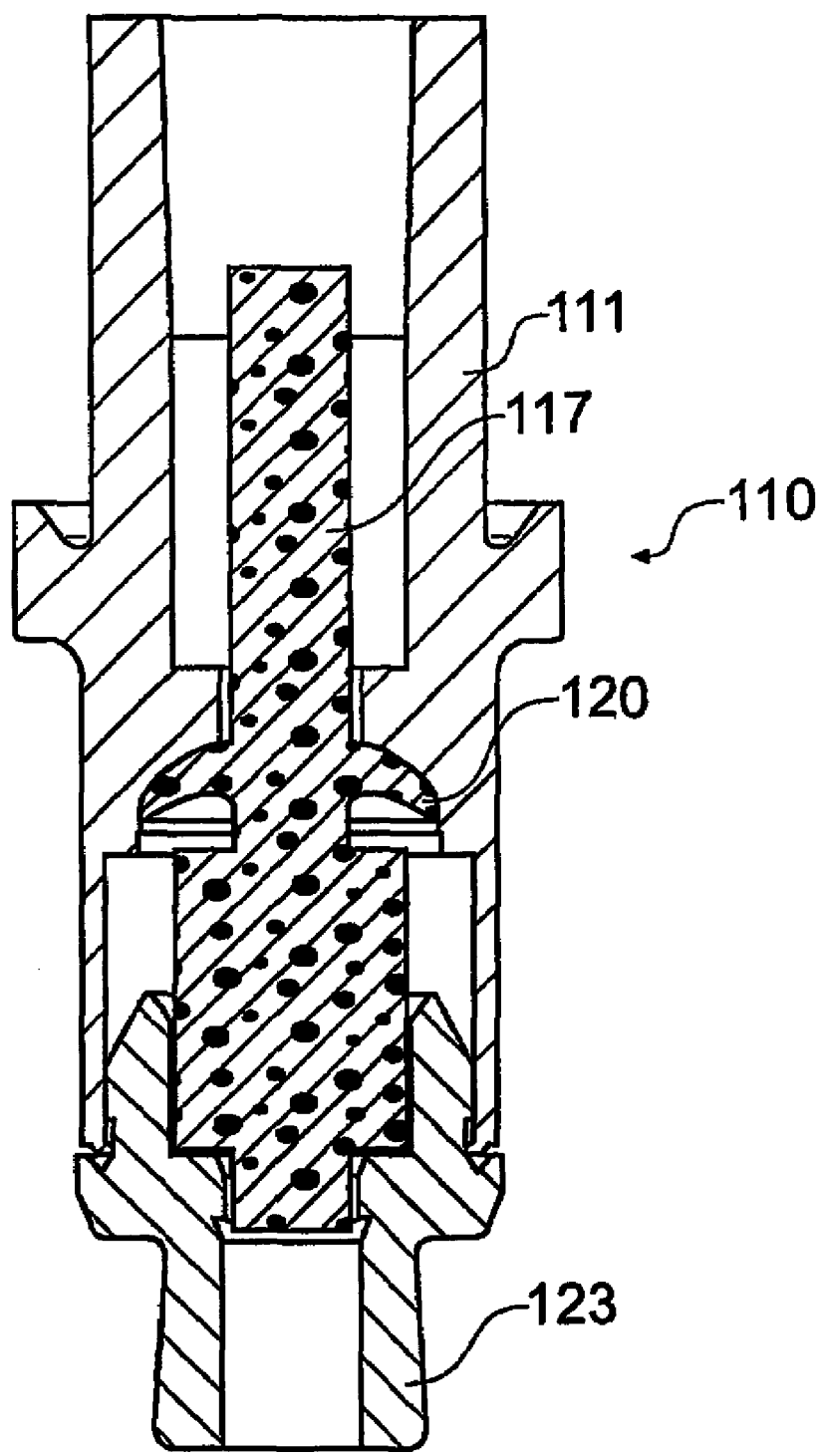
Figure 12:
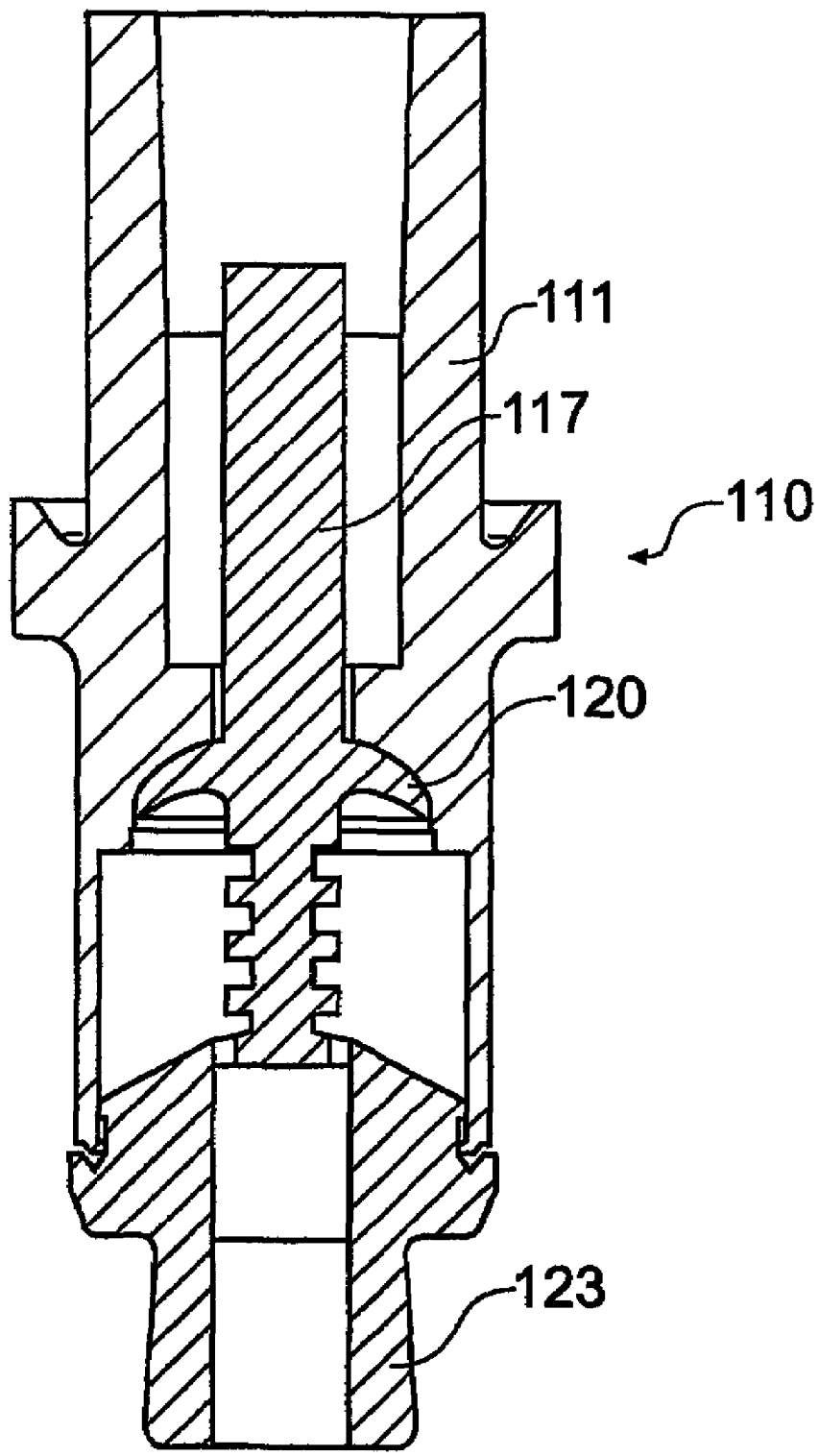
Figure 13:
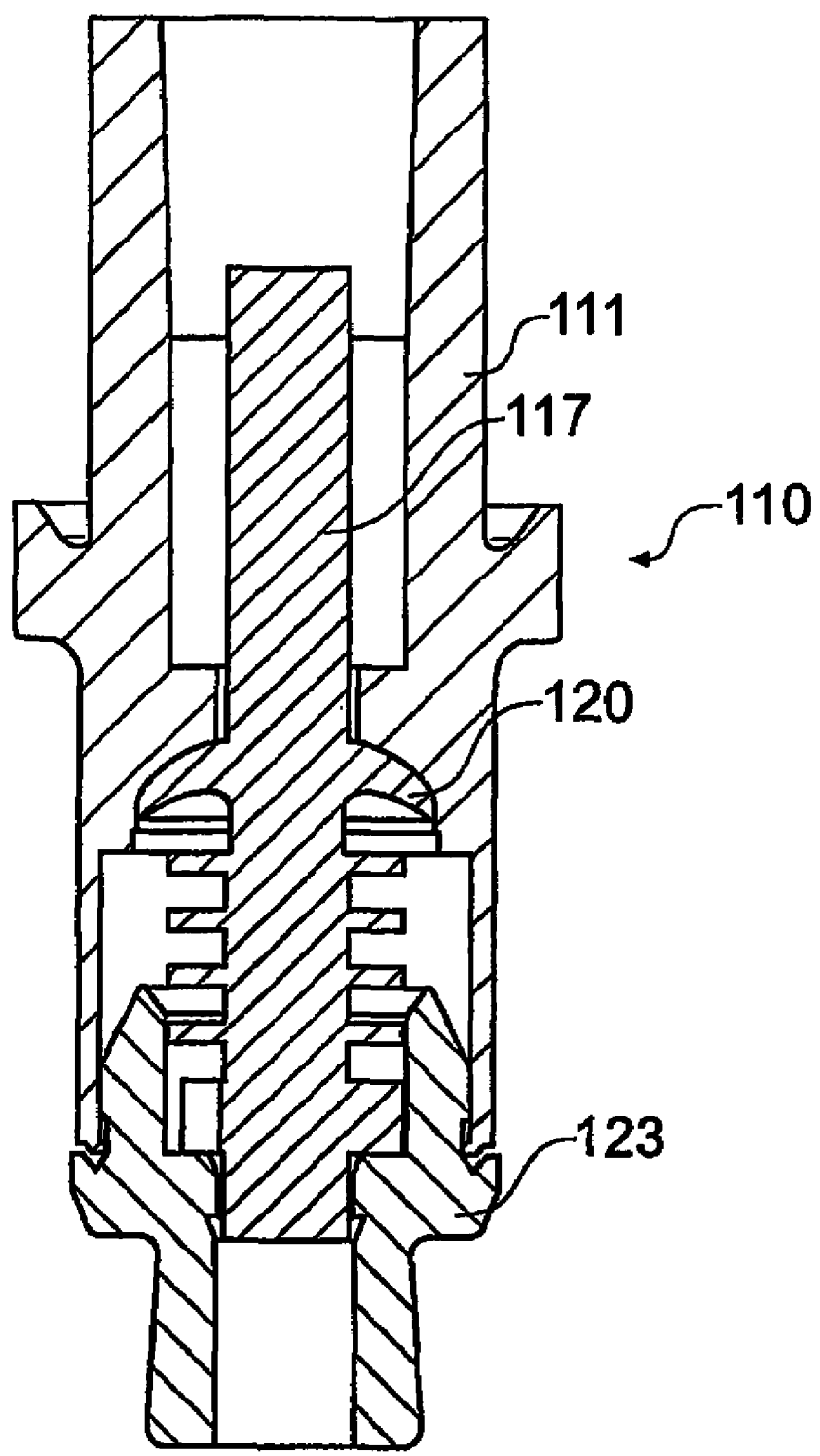

FIGS. 11 to 13 illustrate similar valves to that shown in FIG. 10 except with the variations explained below.

In FIG. 11 the core 117 and resilient projection 120 are made from foam overcoming the need for the spring 122 illustrated in FIG. 10.

In FIG. 12 the core 117, resilient projection 120 and cap 123 are provided as a single component reducing the overall number of components and thus reducing construction costs.

FIG. 13 shows a further alternative arrangement of the valve 110 with the cap 123 provided as a separate component from the hollow body 111.

The skilled person will appreciate that various modifications can be made to the invention described herein. For example, the plunger and closure member may be integrally formed to reduce the number of components required or may be provided as separate components. Furthermore, the channel 11 defined in the closure member of the example of FIGS. 1 to 3 may have only a single inlet or it may have more than two inlets.

Although the closure member is described with regard to FIGS. 1 to 3 as a single component it will be appreciated that it may be formed from a plurality of components. For example, the upper portion 6 of the closure member may be a first component and the lower portion 8 may be a second component. At least a portion of the channel 11 may be defined between the resilient projections or components making up the closure member.

The at least one resilient projection may be provided around the circumference of the closure member's body, or, for example, in an internal channel to form a valve to seal the container. The valve could, for example, be provided in a channel in the lower portion 8 of the closure member shown in FIGS. 1 to 3.

Although many of the examples describe the closure member as having three resilient projections, any number of resilient projections will be suitable for performing the invention.

The resilience of the projections 7, 74, 98, 120 may be chosen such that the medicament is subjected to a pre-compressive load before the projections 7, 74, 98, 120 deflect sufficiently to allow the medicament to flow upwardly through the outlet channel. This is advantageous in that on deflection of the projections 7, 74, 98, 120 the medicament is dispelled into the outlet channel with more energy leading to a quicker and more definite dispensation pattern. In addition, the added energy of the dispelled medicament allows for improved spray formation where the medicament is passed through a spray pattern block or similar.

The resilience of the projections 7, 74, 98, 120 can be selected to any desired level to obtain release of medicament at any desired predetermined pressure. The resilience of the projections 7, 74, 98, 120 may be varied by appropriate selection of materials from which the projections are made, the thickness of the projections and/or the profile of the projections for example.

The container and dispenser described above may be arranged to dispense a single dose or multi-doses as is well known to a person skilled in the art.

Although the above examples have been described in particular orientations, they can of course all be used in any desired orientation.

The invention claimed is:

1. A dispenser comprising a container for a fluid, the container comprising a casing defining an interior for storage of the fluid and a closure member, and a plunger for displacing the closure member relative to the container, the closure member comprising a body, at least one resilient projection, an outlet port and a sealing portion, the at least one resilient projection sealing the casing in a storage condition, and the outlet port being disposed between the at least one resilient projection and the sealing portion, wherein the sealing portion and the at least one resilient projection are in sealing engagement with the casing, wherein the closure member including the sealing portion is displaceable relative to the casing wherein, in use, displacement of the closure member increases the pressure in the interior of the container and, upon an increase in the pressure of the interior of the container the at least one resilient projection is deflected to accommodate outflow of fluid between the casing and the at least one resilient projection through the outlet port.

2. A dispenser according to claim 1, wherein the at least one resilient projection extends substantially radially outwardly from the body of the closure member in an unbiased condition.

3. A dispenser according to claim 1, wherein the at least one resilient projection, in an unbiased condition, has a larger transverse dimension than the interior of the casing.

4. A dispenser as claimed in claim 1, wherein the at least one resilient projection extends circumferentially around the body of the closure member.

5. A dispenser according to claim 1, wherein the closure member seals with the interior of the casing.

6. A dispenser according to claim 1, wherein the at least one resilient projection comprises three resilient projections.

7. A dispenser according to claim 1, wherein the at least one resilient projection has a conical flange configuration.

8. A dispenser according to claim 1, the sealing portion comprising three sealing portions.

9. A dispenser according to claim 1, wherein the closure member and the sealing portion are connected to each other.

10. A dispenser according to claim 9, wherein said sealing portion extends circumferentially around the body of the closure member.

11. A dispenser according to claim 1, wherein the closure member is displaceable relative to the casing wherein, in use, displacement of the closure member increases the pressure in the interior of the container to a point where deflection of a circumferential extension of said at least one resilient projection occurs to feed the outlet port provided in said body while said sealing portion maintains a seal with said casing.

12. A dispenser according to claim 1, wherein the sealing portion is displaceable relative to the casing wherein, in use, displacement of the sealing portion increases the pressure in the interior of the container.

13. A dispenser as claimed in claim 1, wherein the outlet port further comprises a channel for the outflow of fluid, said channel having at least one inlet port in fluid communication with the interior of the container when said at least one resilient projection is deflected.

14. A dispenser according to claim 13, wherein said channel comprises an interconnected axial conduit and transverse conduit, and the at least one inlet port is defined at each end of the transverse conduit.

15. A dispenser according to claim 1, wherein the closure member is made of an elastomer blend, thermoplastic elastomer or a polymer.

16. A dispenser according to claim 15, wherein the elastomer has a Poisson's ratio of less than or equal to 0.5.

17. A dispenser according to claim 1, wherein the closure member has a closed cell foam structure.

18. A dispenser according to claim 1, wherein said container is a vial for medicament.

19. A dispenser according to claim 1, wherein said plunger is designed for displacing the closure member and the at least one sealing portion relative to the container.

20. A dispenser according to claim 1, wherein the closure member is separate from the plunger and sealingly engages an end of said plunger in use.

21. A dispenser according to claim 1, wherein the plunger has a conical flange.

22. A dispenser according to claim 1, wherein the plunger has a delivery channel for delivering the outflow of fluid from the outlet port.

23. A container for a fluid, the container comprising a casing defining an interior for storage of the fluid and a closure member, and a plunger for displacing the closure member relative to said casing, the closure member comprising at least one resilient projection and a sealing portion; the closure member being suitable for sealing an outlet port disposed between the at least one resilient projection and the sealing portion, the at least one resilient projection sealing in a storage condition the outlet port, and the sealing portion and the at least once resilient projection are in sealing engagement with the casing, wherein the closure member including the sealing portion is displaceable relative to the casing wherein, in use, displacement of the closure member increases the pressure in the interior of the container and, upon an increase in the pressure of the interior of the container, the at least one resilient projection is deflected to accommodate outflow of fluid between the casing and the at least one resilient projection through the outlet port.

24. A container according to claim 23, wherein the at least one resilient projection extends circumferentially around the body of the closure member.

25. A container according to claim 23, wherein the at least one resilient projection comprises three resilient projections.

26. A container according to claim 23, wherein the outlet port comprises a channel for the outflow of fluid.

27. A container according to claim 26, wherein said channel comprises an interconnected axial conduit and a transverse conduit.

28. A container according to claim 27 wherein an inlet port is defined at each end of the transverse conduit of the channel.

29. A container according to claim 23, wherein the sealing portion has a convex exterior surface.

30. A container according to claim 23, wherein the sealing portion comprises three sealing portions.

31. A container according to claim 23, wherein the at least one resilient projection further comprises a plurality of resilient projections which each have a conical flange configuration.

32. A container according to claim 23, wherein said closure member comprises, on a common body, said at least one resilient projection and said sealing portion.

33. A container according to claim 23, wherein there are a plurality of each of said at least one resilient projection and sealing portions on said body.

* * * * *